United States Patent [19]
Atkinson, Jr. et al.

[11] Patent Number: 5,382,695
[45] Date of Patent: * Jan. 17, 1995

[54] METHOD FOR DMTDA PRODUCTION

[75] Inventors: E. Earl Atkinson, Jr., Greenwell Springs; Robert A. Schaerfl, Jr.; Edward A. Burt, both of Baton Rouge, all of La.

[73] Assignee: Albemarle Corporation, Richmond, Va.

[ * ] Notice: The portion of the term of this patent subsequent to Apr. 12, 2011 has been disclaimed.

[21] Appl. No.: 708,471

[22] Filed: May 31, 1991

[51] Int. Cl.$^6$ .......................................... C07C 319/14
[52] U.S. Cl. .................................................... 564/440
[58] Field of Search .................... 564/440; 568/57; 502/33, 224, 225; 423/471

[56] References Cited

U.S. PATENT DOCUMENTS

| | | | |
|---|---|---|---|
| 4,594,453 | 6/1986 | Ranken et al. | 564/440 |
| 4,670,597 | 6/1987 | Ranken et al. | 564/440 |
| 4,670,598 | 6/1987 | Davis | 564/440 |
| 4,731,446 | 3/1988 | Pearson et al. | 544/281 |
| 4,825,002 | 4/1989 | Davis | 564/438 |

FOREIGN PATENT DOCUMENTS 1072605 6/1967 United Kingdom .

Primary Examiner—Peter O'Sullivan
Attorney, Agent, or Firm—Richard J. Hammond

[57] ABSTRACT

Thioalkylated aromatic amines are prepared by reacting a mixture of an aromatic amine, an organic disulfide and a Lewis acid or organometallic catalyst to form a product mixture and adding to said product mixture a heavy, miscible organic base or a combination of a heavy, miscible organic base and a poly(oxyalkylene)polymer.

17 Claims, No Drawings

METHOD FOR DMTDA PRODUCTION

This invention relates, broadly, to an improved process for the production of alkylated or thioalkylated aromatic diamines. More specifically, this invention relates to an improved process for the production of dimethylthiotoluenediamine (DMTDA).

BACKGROUND OF THE INVENTION

As disclosed in U.S. Pat. No. 4,594,453 (Ranken et al.), it is known that various (hydrocarbylthio) aromatic amines are useful as intermediates in the preparation of biologically active materials, polyurethanes, etc., and they can be prepared by reacting an aromatic amine with a hydrocarbyl disulfide in the presence of a Lewis acid catalyst. The preferred catalysts of Ranken et al. are metal halides, such as aluminum chloride, boron trifluoride, boron trichloride, ferric chloride and zinc chloride.

U.S. Pat. No. 4,670,597 (Ranken et al.) discloses the preparation of (hydrocarbylthio) aromatic amines by the hydrocarbylthiolation of aromatic monoamines with a hydrocarbyl disulfide in the presence of Lewis acid catalysts selected from hydrogen iodide, ammonium iodide, and copper iodide.

U.S. Pat. No. 4,751,330 (Davis) discloses the preparation of (hydrocarbylthio) aromatic amines by the hydrocarbylthiolation of aromatic amines in the presence of metal or metal halide catalysts, with particularly good results noted with the use of copper, zinc, or ferric, ferrous, or aluminum chloride.

U.S. Pat. No. 4,825,002 (Davis) discloses the removal of a Lewis acid contaminant from a (hydrocarbylthio)aromatic amine by mixing a solid alkali metal hydroxide with a solution of the Lewis acid in the (hydrocarbylthio)aromatic amine, preferably at about 110°–120° C., and then filtering the solids from the mixture.

OBJECTS OF THE INVENTION

In the present preparation of DMTDA, toluenediamine is reacted with dimethyl disulfide in the presence of copper iodide, under pressure of about 25 psig, to form monomethylthiotoluenediamine (MMTDA) and DMTDA, successively. Under present procedure for the preparation of DMTDA, less than desired yields of the final product are achieved. This is due to the reversibility of the thioalkylation step of the process under the temperature conditions of the product recovery portion of the process. This thermal decomposition of the desired product occurs even during relatively short periods of product recovery. In addition, contemporary methods utilized to decrease decomposition, such as lowering the reaction temperature or lowering the catalyst concentration (i.e., via a catalyst precipitation/centrifugation system), were cumbersome and expensive. Centrifugation systems require further processing to repackage the collected catalyst wastes and a means of incinerating such wastes. The present invention allows for the convenient removal of used catalysts by providing for liquid wastes that may be pumped directly to waste reclamation and disposal units.

According to the present invention, decomposition due to reversal of the thioalkylation step, and the resulting loss of product yield, can be prevented by introduction of a catalyst inhibitor into the reaction mixture following the reaction portion of the process.

Accordingly, an object of this invention is to provide an improved process for the production of thioalkylated aromatic diamines.

Another object of this invention is to increase the yields of dimethylthiotoluenediamine formed in the presence of a Lewis acid or organometallic catalyst.

A further object of this invention is to provide a process for the formation of dialkylthiotoluenediamines in which the reversion to monoalkylthiotoluenediamines is minimized.

Still another object of this invention is to provide a process which allows catalyst wastes to be more conveniently removed for recycling or disposal.

DESCRIPTION OF THE PREFERRED EMBODIMENTS

In accordance with the present invention, an aromatic amine is reacted with an organic disulfide in the presence of a catalyst resulting in the formation of hydrocarbylthio aromatic amines.

Aromatic amines utilizable in the practice of the above-mentioned hydrocarbylthiolation process include compounds having at least one amino group attached to a carbocyclic or heterocyclic ring of an aromatic compound containing one or more simple and/or fused rings, such as benzene, naphthalene, anthracene, pyrrole, pyridine, indole, etc. The process may also utilize reactive heterocyclic amines, such as pyrrole, indole, imidazole, etc. The compounds may bear no substituents other than the required amino group(s) or they may bear substituents which are inert to the reaction conditions, such as one or more additional amino groups or substituents such as chloro, fluoro, alkyl, aryl, alkaryl or aralkyl groups on any positions other than those substituted by hydrocarbylthio groups. Examples of useful compounds include 4,4'-methylenedianiline, 4-(phenylthio)aniline, 2-aminobiphenyl, 4-phenoxyaniline, aminobenzenes containing one or two amino groups, such as aniline, 4-butylaniline, 4-methylaniline, 4-chloroaniline, 2-ethylaniline, N-methylaniline, 2,4- and 2,6-diaminotoluenes, 2,6-diamino-1-ethylbenzene, etc.

Organic disulfides which may be reacted with the aromatic amines include saturated and unsaturated aliphatic, cycloaliphatic and aromatic disulfides in which the hydrocarbyl groups optionally bear inert substituents, such as chloro substituents. Examples of such substituents are methyl, ethyl, propyl, n-butyl, sec-butyl, tert-butyl, 2-chlorophenyl, cyclopentyl, cyclohexyl, phenyl, benzyl, p-tolyl and p-chlorophenyl disulfides, etc. The hydrocarbyl disulfide component of the reaction mixture is generally included in at least the stoichiometric amount required to produce the desired hydrocarbylthio aromatic amine. For example, at least one equimolar amount is used when a mono(hydrocarbylthio)aromatic amine is desired and at least two equimolar amounts are used when a di(hydrocarbylthio)aromatic amine is desired.

The reaction of the aromatic amine with the organic disulfide is generally conducted at a temperature in the range of about 20° C. to 300° C. and at a pressure of atmospheric up to about 1000 psi in the presence of a catalyst. Suitable catalysts are Lewis acid catalysts, such as metal halides. Examples of such Lewis acid catalysts are copper chloride, copper bromide, copper iodide, ammonium iodides, hydrogen iodide, zinc iodide, ferrous iodide, cobaltous iodide, aluminum chloride, boron trifluoride, ferric chloride, zinc chloride, zinc iodide, etc. Organometallic compounds derived from the reaction of the aromatic amine with the metal alkyls and reactive metals, such as aluminum, may also be utilized.

In conducting the (hydrocarbylthio)alkylation process, it is generally preferred to (1) heat a mixture of the catalyst and aromatic amine at a suitable temperature, e.g., about 100°-200° C.; and then (2) continue to heat the reaction mixture at reflux temperature after the disulfide has been added to effect a hydrocarbylthiation process while removing evolved hydrocarbyl thiol byproduct from the reaction vessel. However, it is also satisfactory to conduct the process by simply mixing the catalyst and reactants together and heating them to reflux temperature. An inert solvent may be employed if desired, but is unnecessary.

Recovery of the desired product, di(thioalkyl)aromatic diamine(s), may be achieved by conventional heating methods. However, due to the reversibility of the above-mentioned thioalkylation process, recovery flashes in the presence of the Lewis acid catalyst lead to decomposition of the desired product to the corresponding monothioalkylated aromatic diamine. To slow the reverse reaction during product recovery requires lowering the recovery temperature or lowering the catalyst concentration. Physical catalyst separation methods, such as catalyst precipitation/centrifugation, are possible, but impractical. Therefore, it is prudent to utilize a means of inhibiting the action of the catalyst without the necessity of removing the catalyst from the reaction mixture. Furthermore, it is prudent to utilize a means of inhibiting the catalyst without requiring the desired product to be subjected to longer periods under the thermal conditions of the recovery process.

In accordance with the present invention, a heavy, miscible base or a combination of both a heavy, miscible base and a poly(oxyalkylene)polymer is added to the reaction mixture to serve as an inhibitor to the Lewis acid or organometallic catalyst. In such cases, the heavy, miscible base serves to inhibit the catalyst and the poly(oxyalkylene)polymer serves as a chaser to allow for easier handling of the materials involved. For the purposes of this application, a poly(oxyalkylene)polymer shall mean an oxygen-containing alkylene polymer. To be suitable for this method, bases and/or mixtures of bases and poly(oxyalkylene)polymers must be sufficient to inhibit the catalyst and must be soluble in organic solvents. In addition, any bases or poly(oxyalkylene)polymers involved should have a boiling point such that it may not be removed from the reaction mixture prior to the recovery of the desired product. Various amines may be utilized as the base in this process.

Such amines may be chosen from primary, secondary or tertiary alkyl amines, alkyl diamines, aryl amines, polyalkylene amines and poly(oxyalkylene) amines.

Examples of useful alkyl amines include ethyl amine, 1-methyl ethylamine, 1-methyl propylamine, 1-ethyl propylamine, 1-ethyl butylamine, 1-methyl butylamine, 1-methyl pentylamine, 1-ethyl pentylamine, 1-propyl pentylamine, 1-methyl heptylamine, 1-ethyl heptylamine, n-propylamine, isopropylamine, n-butylamine, sec-butylamine, tert-butylamine, isobutylamine, n-pentylamine, isopentylamine, tert-pentylamine, n-hexylamine, n-heptylamine, etc.

Examples of useful alkyl diamines include 1,3-propanediamine, 1,4-butanediamine, 1,5-pentanediamine, 1,6-hexanediamine, etc.

Examples of polyoxyalkylene amines would include poly(oxyalkylene) amines containing repeating oxyalkylene components from $C_2$-$C_6$, such as poly(oxypropylene) amines of the formula $NH_2CH(CH_3)CH_2$—$[OCH_2CH(CH_3)]_nNH_2$ and poly(oxybutylene) amines of the formula $NH_2(CH_2)_4$—$[OCH_2CH_2CH_2CH_2]_nNH_2$. JEFFAMINE ® D400 (polyoxyalkyleneamine), JEFFAMINE ® D600 (polyoxyalkyleneamine), JEFFAMINE ® D2000 (polyoxyalkyleneamine), JEFFAMINE ® D3000 (polyoxyalkyleneamine), and JEFFAMINE ® D4000 (polyoxyalkyleneamine) are examples of useful poly(oxyalkylene)diamines. JEFFAMINE ® amines are products of Texaco, Inc.

Various amines, as described above, may be useful in the present invention. Those of lower molecular weight (i.e., less than 200), such as diisopropylamine or ethylcyclohexylamine, however, may be lost during thermal product recovery methods due to their lower boiling temperatures. In addition, other bases, such as sodium hydroxide, tetraethylpentamine, 4,4,10-trioxatridecane-1,13-diamine, isobutylpentamine and methylene dianiline, were found unacceptable as they led to formation of undesired solids in the reaction medium.

In addition, various poly(oxyalkylene)polymers may be utilized in the present invention. As mentioned above, the poly(oxyalkylene)polymers must be soluble in the organic compound of the reaction and product mixtures and should have a boiling point such that it will not be removed from the reaction mixture prior to the recovery of the desired product.

Examples of useful oxygen-containing alkylene polymers include alkylene diols such as 1,2-octanediol, 1,2-decanediol, 1,3-decanediol, etc., and alkylene ether glycols such as polyethylene glycol $H(OCH_2CH_2)_nOH$, polypropylene glycol, polybutylene glycol and poly(1,3-butylene)glycol. Also useful are alkyl- or aryl-terminated alkylene ether polymers, wherein the aryl terminating group is substituted or unsubstituted, such as those seen in the Brij ® polyoxyethylene series (ICI Corp.), the Lipopeg ® series (Lipo Chemicals), the Atlas ® G series (ICI Corp.) and the Igepal ® CO series (GAF Corp.).

The examples that follow exemplify the present invention, but are not intended to limit the scope of the invention.

EXAMPLES

In the following product recovery tests (Comparative Example and Examples 1–7), a continuous flash unit was utilized. In these tests, decomposition of the desired product will be indicated by comparisons of the amounts of DMTDA and MMTDA going into and out of the product recovery phase. Effective inhibition of the CuI catalyst (in the presence of a heavy, miscible organic base) will be shown by a decreased loss of DMTDA and a decrease in the amount of MMTDA created.

In each example, the continuous flash system was prepared by heating the flash pot to a temperature of about 185° C. and a cooling bath to 70° C. The system was purged with nitrogen and pot pressure was maintained below 1 mm Hg. A known weight of reaction crude [containing dimethyldisulfide (DMDS), MMTDA, DMTDA and trimethylthiometaphenylenediamine (TMMPDA)] was fed continuously into the feed pot, resulting in a residence time of about 5.5 minutes. The percent composition of DMTDA and MMTDA in the distillate were determined to indicate percentage of product recovery.

COMPARATIVE EXAMPLE 485.10 g of reaction crude was placed in the product flash pot. The reaction crude consisted of 1.14 area % DMDS, 1.97 area % MMTDA, 96.23 area % DMTDA and 0.66 area % TMTDA. Upon completion of the product flash, the 303.5 g of distillate recovered was determined to contain 4.40 area % DMDS, 4.61 area % MMTDA, 90.60 area % DMTDA and 0.39 area % TMTDA.

EXAMPLES 1-7

In each of the following examples, known amounts of JEFFAMINE® D-2000 (polyoxyalkyleneamine), a product of Texaco, Inc., was introduced into the flash pot of the continuous flash unit prior to the introduction of the reaction crude (feed) to inhibit reversion of DMTDA to MMTDA during the product recovery steps. The table provided below indicates the amounts of MMTDA and DMTDA in the feed and the amounts of each in the recovered distillate (out).

| EXAMPLE NO. | 1 | 2 | 3 | 4 | 5 | 6 | 7 |
|---|---|---|---|---|---|---|---|
| % JEFFAMINE ® D-2000 AMINE IN FEED | 2.06 | 5.94 | 5.95 | 0 | 0 | 0 | 0 |
| DMTDA in (g) | 441.1 | 447.5 | 445.2 | 443.7 | 444.3 | 443.0 | 435.5 |
| MMTDA in (g) | 9.0 | 9.2 | 9.1 | 9.1 | 9.1 | 9.1 | 8.9 |
| DMTDA out (g) | 438.9 | 437.5 | 434.8 | 425.1 | 428.9 | 423.9 | 429.1 |
| MMTDA out (g) | 10.6 | 10.7 | 10.3 | 15.3 | 16.5 | 16.0 | 15.2 |
| % DMTDA Decomp. | 0.5 | 2.2 | 2.3 | 4.2 | 3.5 | 4.3 | 1.5 |
| % MMTDA Accum. | 17.8 | 16.3 | 13.2 | 68.1 | 81.3 | 75.8 | 70.8 |

DMTDA Decomp. = (In-Out)/In
MMTDA Accum. = (Out-In)/In

What is claimed:

1. In a process for producing thioalkylated toluene diamines comprising forming a reaction mixture comprising (a) a toluene diamine having no substituents other than the required amino groups or having one or more substituents which are inert to the reaction conditions, (b) an organic disulfide, and (c) a Lewis acid catalyst or organometallic catalyst, said reaction mixture producing a product mixture from which the desired thioalkylated toluene aliamines are removed by thermal product recovery methods, the improvement comprising adding to said product mixture a heavy, miscible organic base having a molecular weight of between about 200 and about 4,000, the heavy, miscible organic: base being chosen from the group of primary, secondary or tertiary amines, alkyl diamines aryl amines, polyalkylene amines or poly(oxyalkylene)amines, or a combination of said heavy, miscible organic base and an oxygen-containing compound selected from the group consisting of alkylene diol, alkylene ether glycol, alkyl-terminated alkylene ether polymer and aryl-terminated alkylene ether polymer, said oxygen-containing compound having the following properties:
   i) it is soluble in the compounds of the reaction and product mixtures, and
   ii) it has a boiling point such that the compound will not be removed from the reaction mixture prior to the recovery of the product.

2. The process of claim 1 in which the heavy, miscible organic base has a molecular weight of between about 350 and about 2,100.

3. The process of claim 1 in which the heavy, miscible organic base is a polyoxyalkylene amine.

4. The process of claim 1 in which the oxygen-containing compound has a molecular weight of between about 400 and about 1,000.

5. The process of claim 1 in which the oxygen-containing compound has a molecular weight of between about 500 and about 700.

6. The process of claim 1 in which the combination of heavy, miscible organic base and oxygen-containing compound is in a ratio of heavy, miscible organic base to oxygen-containing compound of between about 100 to 0 and about 0 to 100.

7. The process of claim 1 in which the combination of heavy, miscible organic base and oxygen-containing compound is in a ratio of heavy, miscible organic base to oxygen-containing compound of between about 75 to 25 and about 25 to 75.

8. The process of claim 1 in which the combination of heavy, miscible organic base and oxygen-containing compound is in a ratio of heavy, miscible organic base to oxygen-containing compound of between about 60 to 40 and about 40 to 60.

9. The process of claim 1 in which the combination of heavy, miscible organic base and oxygen-containing compound is in a ratio of heavy miscible organic base to oxygen-containing compound of about 50 to 50.

10. The process of claim 1 in which the aromatic amines are phenylene diamines.

11. The process of claim 1 in which the thioalkylated aromatic amines are metaphenylenediamines.

12. The process of claim 1 in which the thioalkylated aromatic amines are toluenediamines.

13. The process of claim 1 in which the organic disulfide contains from 1 to 6 carbon atoms.

14. The process of claim 1 in which the organic disulfide is dimethyl disulfide.

15. The process of claim 1 in which the Lewis acid catalyst is aluminum chloride.

16. The process of claim 1 in which the Lewis acid catalyst is copper iodide.

17. The process of claim 1 in which the Lewis acid catalyst is zinc chloride.

* * * * *